(12) United States Patent
Danen et al.

(10) Patent No.: US 10,338,002 B1
(45) Date of Patent: Jul. 2, 2019

(54) METHODS AND SYSTEMS FOR SELECTING RECIPE FOR DEFECT INSPECTION

(71) Applicant: KLA-Tencor Corporation, Milpitas, CA (US)

(72) Inventors: Robert M. Danen, San Jose, CA (US); Shuo Sun, Fremont, CA (US); Thomas Boatwright, Milpitas, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/411,719

(22) Filed: Jan. 20, 2017

Related U.S. Application Data

(60) Provisional application No. 62/289,870, filed on Feb. 1, 2016, provisional application No. 62/410,669, filed on Oct. 20, 2016.

(51) Int. Cl.
*H01L 21/00* (2006.01)
*G01N 21/88* (2006.01)
*G01N 21/95* (2006.01)
*G06T 7/00* (2017.01)
*H01L 21/66* (2006.01)

(52) U.S. Cl.
CPC ..... *G01N 21/8851* (2013.01); *G01N 21/9505* (2013.01); *G06T 7/0004* (2013.01); *H01L 22/20* (2013.01); *G01N 2021/8887* (2013.01); *G06T 2207/30148* (2013.01)

(58) Field of Classification Search
None
See application file for complete search history.

(56) References Cited

U.S. PATENT DOCUMENTS

| | | | |
|---|---|---|---|
| 3,178,602 A | 4/1965 | Meixner | |
| 3,181,042 A | 4/1965 | Stock | |
| 4,315,152 A | 2/1982 | Smith | |
| 6,057,553 A | 5/2000 | Khursheed et al. | |
| 6,307,312 B1 | 10/2001 | Tanaka | |
| 6,317,514 B1 * | 11/2001 | Reinhorn | G01N 21/95692 250/224 |
| 6,777,676 B1 * | 8/2004 | Wang | G01N 23/225 250/306 |
| 6,825,119 B1 * | 11/2004 | Lin | G01N 21/9501 257/E21.527 |

(Continued)

FOREIGN PATENT DOCUMENTS

WO 2016009433 A1 1/2016

OTHER PUBLICATIONS

"Failure Analysis of Integrated Circuits" by Wagner, Lawrence, Jan. 1999.*

(Continued)

*Primary Examiner* — Evren Seven
(74) *Attorney, Agent, or Firm* — Suiter Swantz pc llo (57) ABSTRACT

Methods and systems for selecting optical modes suitable for defect inspection are disclosed. A method may include: scanning a full-stack wafer of the particular type utilizing a set of optical modes to obtain a set of full-stack wafer images; and de-processing the full-stack wafer to produce a de-processed wafer based on a location of a potential defect of interest indicated by the set of full-stack wafer images to facilitate selection of optical modes suitable for defect inspection of wafers of the particular type.

32 Claims, 8 Drawing Sheets

(56) References Cited

U.S. PATENT DOCUMENTS

| | | | |
|---|---|---|---|
| 7,075,092 | B2 | 7/2006 | Winkler et al. |
| 7,663,327 | B2 | 2/2010 | Bhatt et al. |
| 8,455,838 | B2 | 6/2013 | Shadman et al. |
| 8,698,094 | B1 | 4/2014 | Sears et al. |
| 2005/0285106 | A1* | 12/2005 | Kane ................ G01N 21/68 257/48 |
| 2006/0197030 | A1 | 9/2006 | Buijsse et al. |
| 2008/0153183 | A1* | 6/2008 | Mathews .......... H01L 21/02068 438/14 |
| 2008/0153185 | A1* | 6/2008 | Mathews .......... H01L 21/02079 438/16 |
| 2008/0279444 | A1 | 11/2008 | Fischer et al. |
| 2014/0139830 | A1 | 5/2014 | Lange |
| 2014/0212023 | A1 | 7/2014 | Fujii et al. |
| 2014/0354983 | A1 | 12/2014 | Kolchin et al. |

OTHER PUBLICATIONS

"A Study on Chemical Delayering Method to Expose Tunnel Window and Oxide in Wafer Fabrication" by Hua et al., Jan. 2002.*
M. Nirkko, et al., "An adjustable focusing system for a 2 MeV H—ion beam line based on permanent magnet quadrupoles", Journal of Instrumentation, Feb. 5, 2013, vol. 8.

* cited by examiner

FIG. 7

METHODS AND SYSTEMS FOR SELECTING RECIPE FOR DEFECT INSPECTION

CROSS-REFERENCE TO RELATED APPLICATIONS

The present application claims the benefit under 35 U.S.C. § 119(e) of U.S. Provisional Application Ser. No. 62/289,870, filed Feb. 1, 2016. Said U.S. Provisional Application Ser. No. 62/289,870 is hereby incorporated by reference in its entirety.

The present application also claims the benefit under 35 U.S.C. § 119(e) of U.S. Provisional Application Ser. No. 62/410,669, filed Oct. 20, 2016. Said U.S. Provisional Application Ser. No. 62/410,669 is hereby incorporated by reference in its entirety.

TECHNICAL FIELD

The disclosure generally relates to the field of inspection, and particularly to inspection of semiconductor devices.

BACKGROUND

Thin polished plates such as silicon wafers and the like are a very important part of modern technology. A wafer, for instance, may refer to a thin slice of semiconductor material used in the fabrication of integrated circuits and other devices. Other examples of thin polished plates may include magnetic disc substrates, gauge blocks and the like. While the technique described here refers mainly to wafers, it is to be understood that the technique also is applicable to other types of polished plates as well. The term wafer and the term thin polished plate may be used interchangeably in the present disclosure.

Wafers are subjects to defect inspections. Tools utilized to perform such inspections are expected to be efficient and effective. It is noted, however, that recent developments in 3D NAND technologies have challenged the efficiency and effectiveness of existing inspection tools. More specifically, because 3D NAND technologies may stack multiple layers vertically on a wafer, inspection tools designed to inspect a single planer layer do not work well when attempting to identify 3D NAND buried defects.

Therein lies a need for providing methods and systems for inspecting buried defects.

SUMMARY

The present disclosure is directed to a method for selecting optical modes and algorithms, which in part comprise the recipe, suitable for defect inspection of a particular type of wafer. The method may include: scanning a full-stack wafer of the particular type utilizing a set of optical modes and algorithms to obtain a set of full-stack wafer images; and de-processing the full-stack wafer to produce a de-processed wafer based on a location of a potential defect of interest indicated by the set of full-stack wafer images to facilitate selection of optical modes and algorithms suitable for defect inspection of wafers of the particular type.

A further embodiment of the present disclosure is a system. The system may include an optical inspection tool configured to obtain optical images of one or more wafers utilizing one or more optical modes. The system may also include an image storage medium and at least one processor in communication with the optical inspection tool. The at least one processor may be configured to facilitate selection of optical modes suitable for defect inspection. The at least one processor may be further configured to: receive a set of full-stack wafer images obtained by the optical inspection tool by scanning a full-stack wafer using a set of optical modes; receive verified defect locations based on at least one of an optical inspection or a scanning electron microscope review of a de-processed wafer, the de-processed wafer being a product of de-processing the full-stack wafer based on a location of a potential defect of interest indicated by the set of full-stack wafer images; and form a recipe for defect inspection to be utilized by the optical inspection tool based on the set of full-stack wafer images and the verified defect locations from the de-processed wafer.

An additional embodiment of the present disclosure is directed to a system. The system may include an optical inspection tool configured to obtain optical images of one or more wafers utilizing one or more optical modes. The system may also include at least one processor in communication with the optical inspection tool. The at least one processor may be configured to facilitate selection of optical modes and algorithms suitable for defect inspection. The at least one processor may be further configured to: receive a set of full-stack wafer images obtained by the optical inspection tool by scanning a full-stack wafer using a set of optical modes and algorithms; receive a set of de-processed wafer images obtained by the optical inspection tool by scanning a de-processed wafer using the set of optical modes and algorithms, the de-processed wafer being a product of de-processing the full-stack wafer based on a location of a potential defect of interest indicated by the set of full-stack wafer images; and form a recipe for defect inspection to be utilized by the optical inspection tool based on the set of full-stack wafer images and the set of de-processed wafer images.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

Figure 1A:
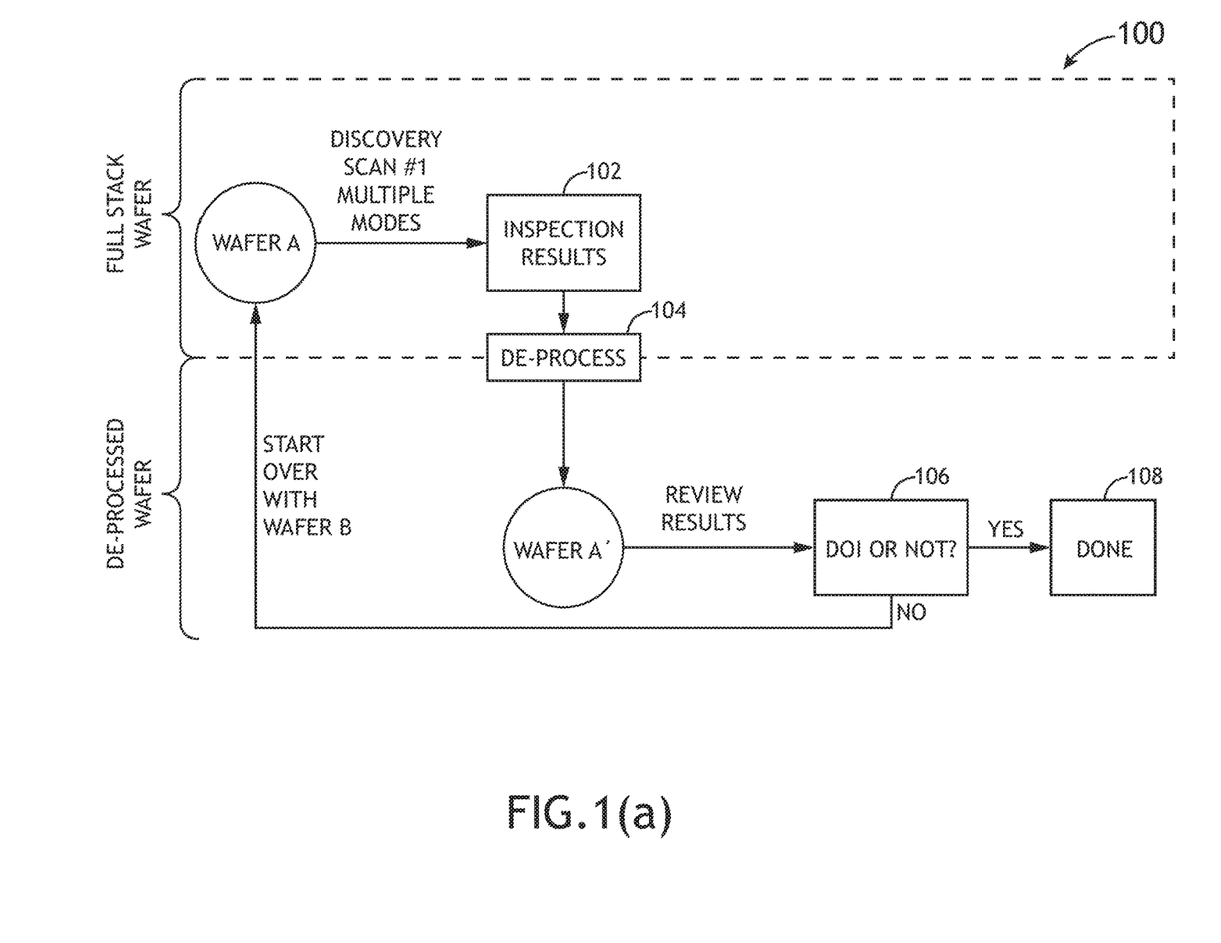
FIG. 1(a) is a flow diagram depicting an inspection method.

Referring generally to FIG. 1(a), a flow diagram depicting an inspection method 100 for buried defects (may be referred to simply as the inspection method 100) is shown. The inspection method 100 may be configured to inspect a target (e.g., a wafer A) that has multiple vertically stacked layers. The inspection method 100 may select a set of (e.g., 5 or more) different optical modes in a step 102 to carry out a discovery scan of the wafer A. The optical modes selected may differ in terms of aperture settings, focus settings, wavelength bands or frequency settings. The inspection method 100 may select a different detection algorithm in the step 102 to carry out a discovery scan of the wafer A. The detection algorithms selected may differ in terms of settings, such as thresholds and filters, or in terms of algorithm methods. Results in the form of a list of defect positions obtained using the different optical modes and different detection algorithms are generated accordingly. The results may include small optical images of the defect and attributes calculated from the images.

It is noted that by carrying out the discovery scan using different optical modes or algorithms, defects that may be buried in different layers of the wafer A may be obtained. If, for example, the discovery scan indicates that a potential defect of interest (or DOI) is located at the bottom layer of the stack, a verification process may be invoked to verify whether the potential DOI indicated by the discovery scan is indeed a DOI of concern. This verification process may be carried out using a de-processed wafer. This verification process may be carried out also by performing electrical tests of the wafer after processing of circuits completes.

Figure 1B:
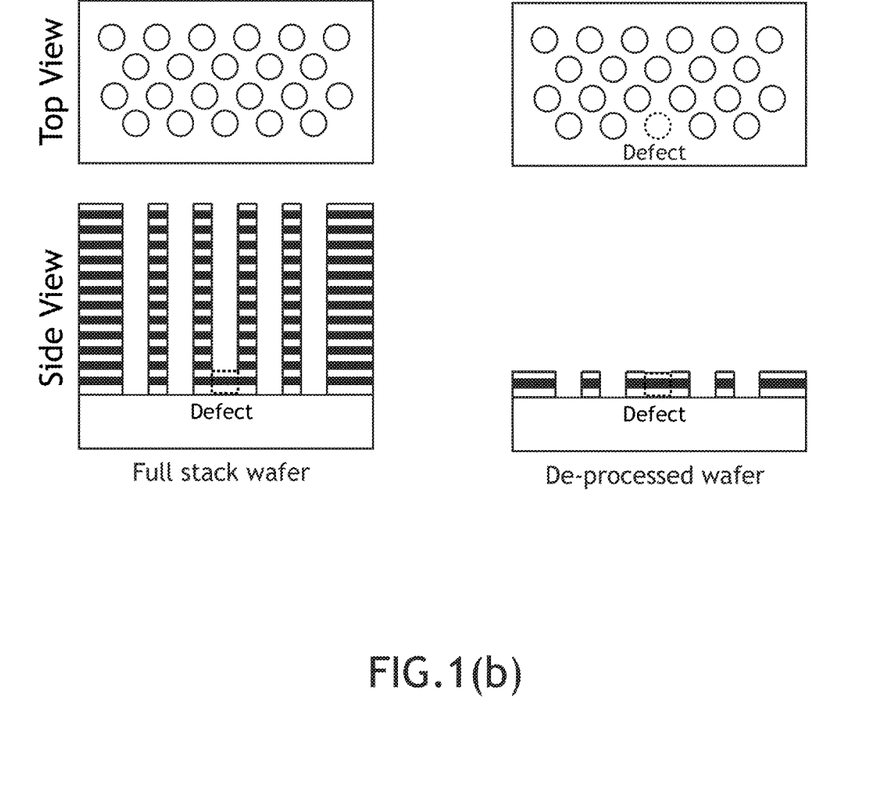
FIG. 1(b) is a diagram comparing a full stack and de-processed wafer.

A de-processed wafer is a wafer with certain layers removed. FIG. 1(b) depicts a diagram of full stack and de-processed wafer. The defect is the extra material delineated by the dotted lines. Referring to the example depicted above, if the discovery scan indicates that a potential DOI is located at the bottom layer of the stack, the layers above the bottom layer of the stack may be removed from the wafer A in a de-process step 104 to provide a de-processed wafer A'. The de-process step 104 may remove material from the entire wafer surface or from selected sites determined from inspections of full-stack wafer. The de-process step 104 may remove material from above the defect as shown in FIG. 1(b) or from the side of the defect. The de-processed wafer A' may then be reviewed in a step 106 against the discovery scan. If the review reveals that the potential DOI indicated by the discovery scan is not a true DOI of concern, it may suggest that the optical modes selected to perform the discovery scan were ineffective for the wafer A and the inspection method 100 may repeat from the step 102 again by selecting a different set of optical modes or algorithms. Eventually, when the review reveals that the potential DOI indicated by the discovery scan is indeed a true DOI of concern, the inspection method 100 may terminate in a step 108 and the optical modes used to perform the discovery scan may be identified as the optical modes to be utilized for subsequent inspections of wafers having the same type as the wafer A.

It is noted that the inspection method 100 described above is essentially configured to identify the set of optical modes suitable for inspecting a certain type of wafer by trial and error. A drawback associated with a trial and error based approach is that the inspection method 100 may take a long time to produce the final result. It is also noted that, for the case where the de-process step 104 is performed on the entire wafer, the inspection method 100 cannot be repeated on the same wafer, as that wafer is effectively destroyed in the de-process step 104. Additional scans must therefore be performed on a new wafer. To help reduce the time and wafers needed to produce the final result, an alternative approach may be taken as depicted in FIG. 2.

Figure 2:
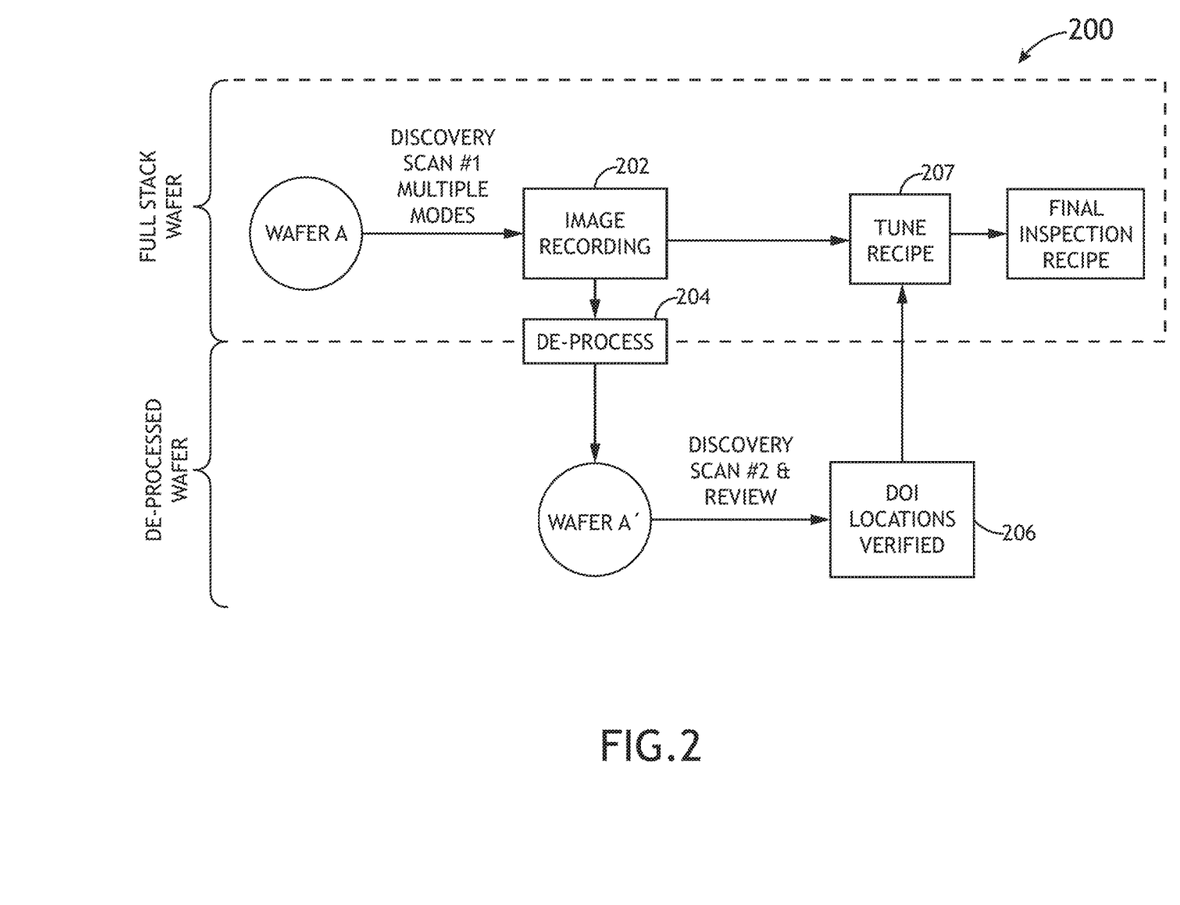
FIG. 2 is a flow diagram depicting an inspection method configured in accordance with an embodiment of the present disclosure.

More specifically, FIG. 2 contains a flow diagram depicting an inspection method 200 for embedded defects (or simply an inspection method 200) configured in accordance with an embodiment of the present disclosure. As depicted in FIG. 2, the inspection method 200 may be configured to inspect a target (e.g., a wafer A) that has multiple vertically stacked layers. The inspection method 200 may select a set of different optical modes in a step 202 to carry out a discovery scan of the wafer A. The optical modes selected may differ in terms of aperture settings, focus settings, wavelength band, and/or frequency settings, and a set of optical images obtained using the different optical modes may be recorded and stored accordingly. The set of optical images can be recorded and stored for all specified areas without first generating an inspection result using an algorithm (e.g., defect locations). Alternatively, an inspection result can be generated for one or more modes with associated algorithms and then these results can define regions to record images for additional discovery scans.

Figure 3:
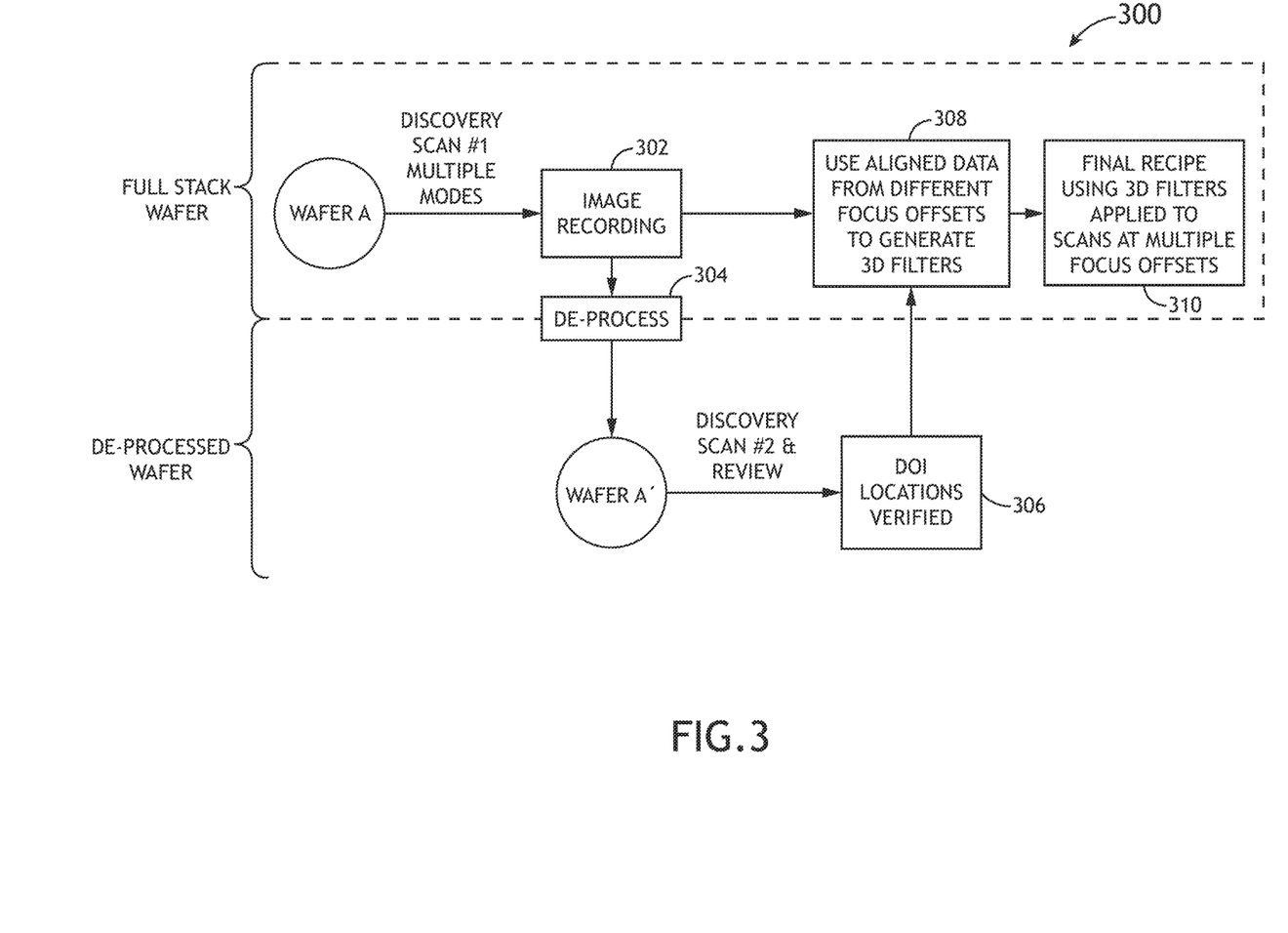
FIG. 3 is a flow diagram depicting still another inspection method configured in accordance with an embodiment of the present disclosure.

FIG. 3 is a flow diagram depicting an inspection method 300 similar to the inspection method 200 described above, but with differences between the various optical modes limited to focus settings only. More specifically, as shown in FIG. 3, the inspection method 300 may be configured to inspect a target (e.g., a wafer A) that has multiple vertically stacked layers. The inspection method 300 may select a set of (e.g., 5 or more) different optical modes in a step 302 to carry out a discovery scan of the wafer A. The optical modes selected may differ in terms of focus settings, and a set of optical images obtained using the different focus settings (i.e., a through-focus stack) may be recorded/stored accordingly.

The wafer A may then be de-processed in a step 304 to provide a de-processed wafer A', which may be scanned again using the same or different set of optical modes to identify defect locations in a step 306. The de-process step 304 may remove material from the entire wafer surface or from selected sites determined from inspections of the full-stack wafer. Using these identified defect locations, the first set of optical images may be aligned in step 308, which may utilize the aligned data from the different focus settings to generate one or more 3D filters. The 3D filters generated in this manner may then be utilized as a part of the final inspection recipe in a step 310 to carry out through-focus stack inspections of wafers having the same type as the wafer A.

Referring back to FIG. 2, the wafer A may be de-processed in a step 204 to provide a de-processed wafer A', which may be scanned again using the same (i.e., same as the optical modes selected in the step 202) or a different set of optical modes to obtain a second set of optical images in a step 206. The second set of optical images may then be used together with the first set of optical images to help tune the inspection recipe in a recipe tuning step 207. The recipe obtained in this manner may then be utilized to perform subsequent inspections of wafers having the same type as the wafer A.

It is contemplated that the recipe tuning step 207 may be carried out in various manners. In some embodiments, for example, the recipe tuning step 207 may be carried out at least partially based on correlations between the signals contained in the second set of optical images and the signals contained in the first set of optical images. This process is further illustrated in FIGS. 4 and 5.

Figure 4:
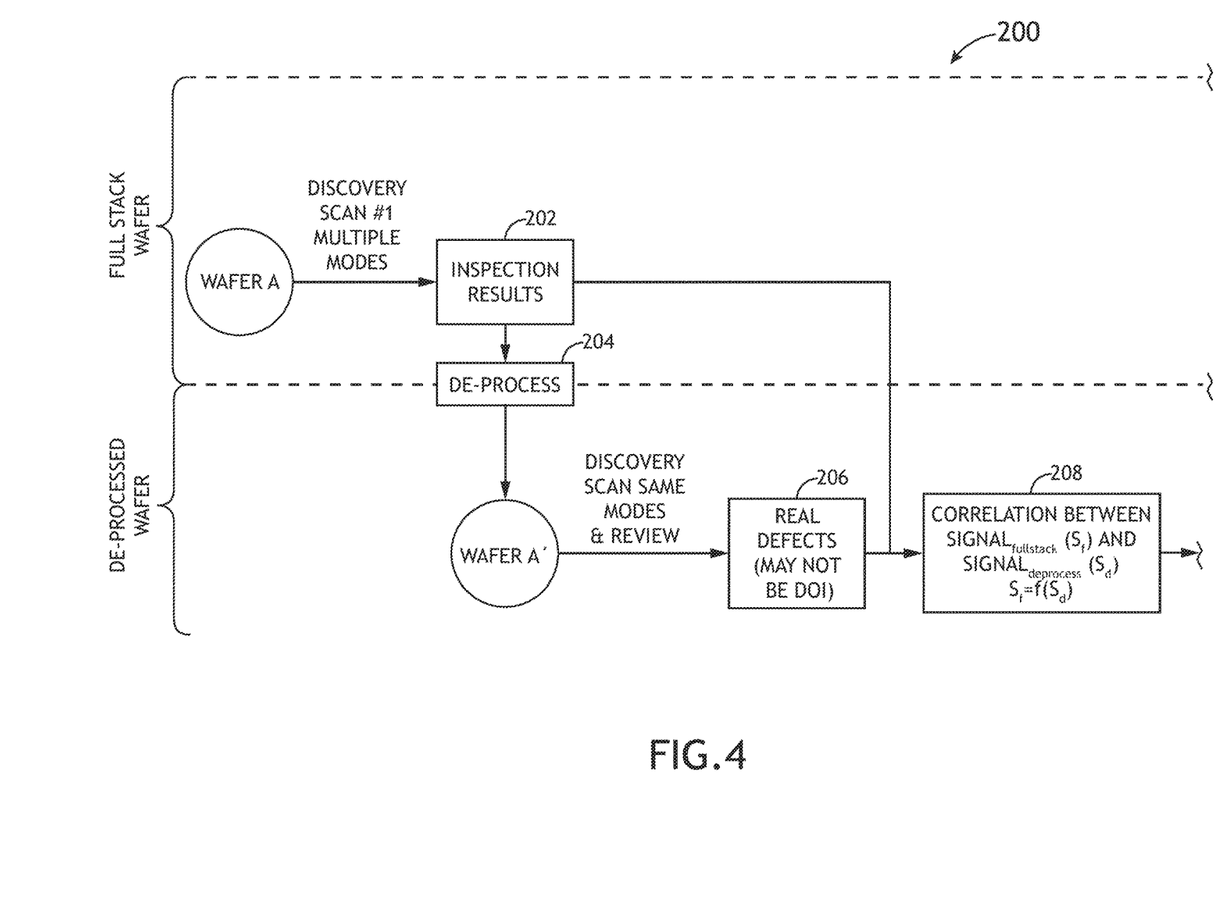
FIG. 4 is a flow diagram depicting a portion of an inspection method configured in accordance with an embodiment of the present disclosure.
Figure 5:
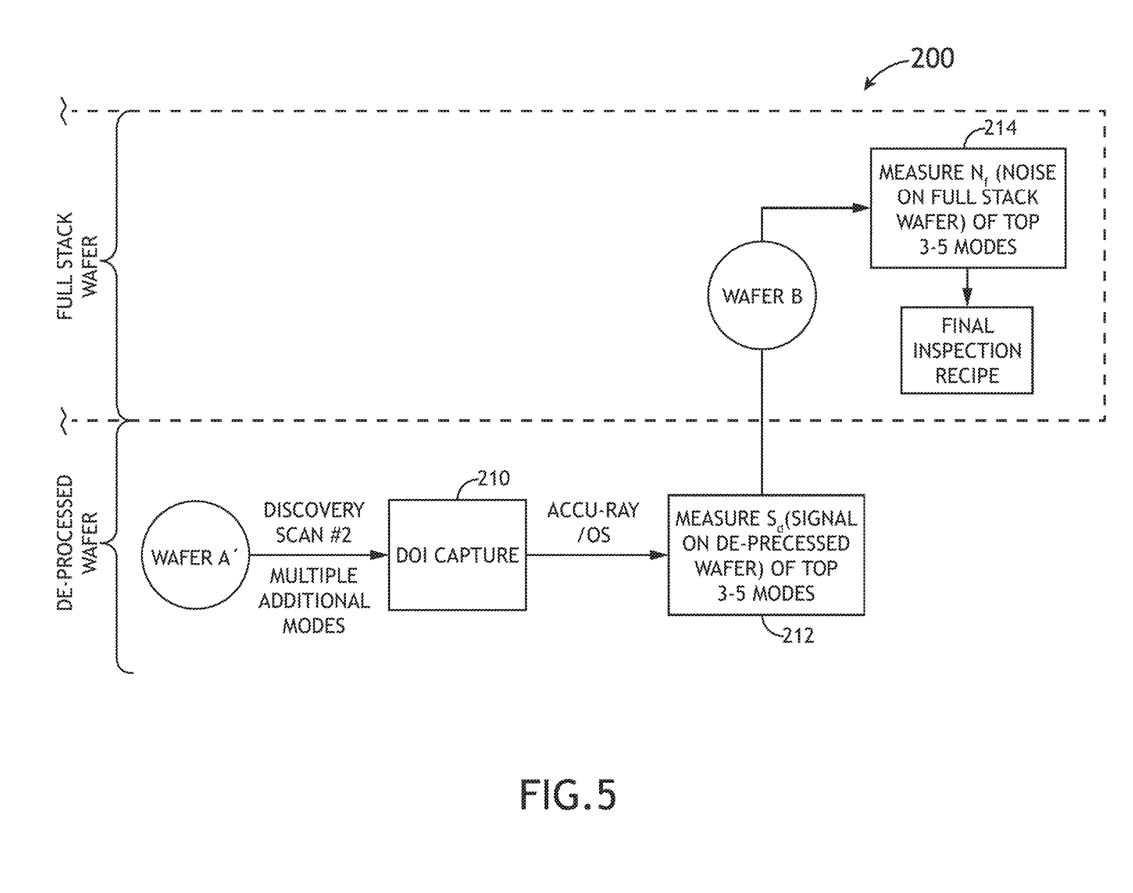
FIG. 5 is a flow diagram depicting a second portion of the inspection method depicted in FIG. 4.

More specifically, as shown in FIG. 4, the signals contained in the second set of optical images, denoted as Signal$_{de\text{-}processed}$, or S$_d$, and the signals contained in the first set of optical images, denoted as Signal$_{full\text{-}stack}$, or S$_f$, may be correlated against each other and the correlation between them, denoted as S$_f$=f(S$_d$), may be obtained in a step 208. The inspection method 200 may continue as depicted in FIG. 5, where DOI signals and the optical noise in the images are measured. The DOI signals may be measured by first capturing the DOI(s) on the de-processed wafer A' using a second set of optical modes in a step 210. In some embodiments, the second set of optical modes may be the same as the first set of optical modes. In some embodiments, however, the second set of optical modes used in the step 210 may include at least one optical mode that is not a member of the first set of optical modes used in the steps 202 and 206. Subsequently, a step 212 may be utilized to measure the signals (Signal$_{de\text{-}processed}$, or S$_d$) obtained from the de-processed wafer A' using the second set of optical modes. The step 212 may also be utilized to filter out some of the optical modes from the second set of optical modes based on their signal-to-noise (S/N) ratios. For instance, in some embodiments, the step 212 may only keep the signals (S$_d$) obtained from the top N-number of (e.g., 3 or 5) optical modes.

Also shown in FIG. 5 there is a noise measurement step 214 that may be utilized to obtain measurements from another wafer B. It is noted that the wafer B and the wafer A may be of the same type. It is also noted that the wafer B is a full-stack wafer (i.e., the wafer B has not been de-processed yet). The full-stack wafer B may be measured in the step 214 using the top N-number of optical modes identified by the step 212. Subsequently, the noise on the full-stack wafer B (denoted as Noise$_{full\text{-}stack}$, or N$_f$) obtained using the top N-number of optical modes may be measured. The noise measurement obtained in this manner may then be considered as a factor in determining inspection recipes for wafers having the same type as the wafer A.

Figure 6:
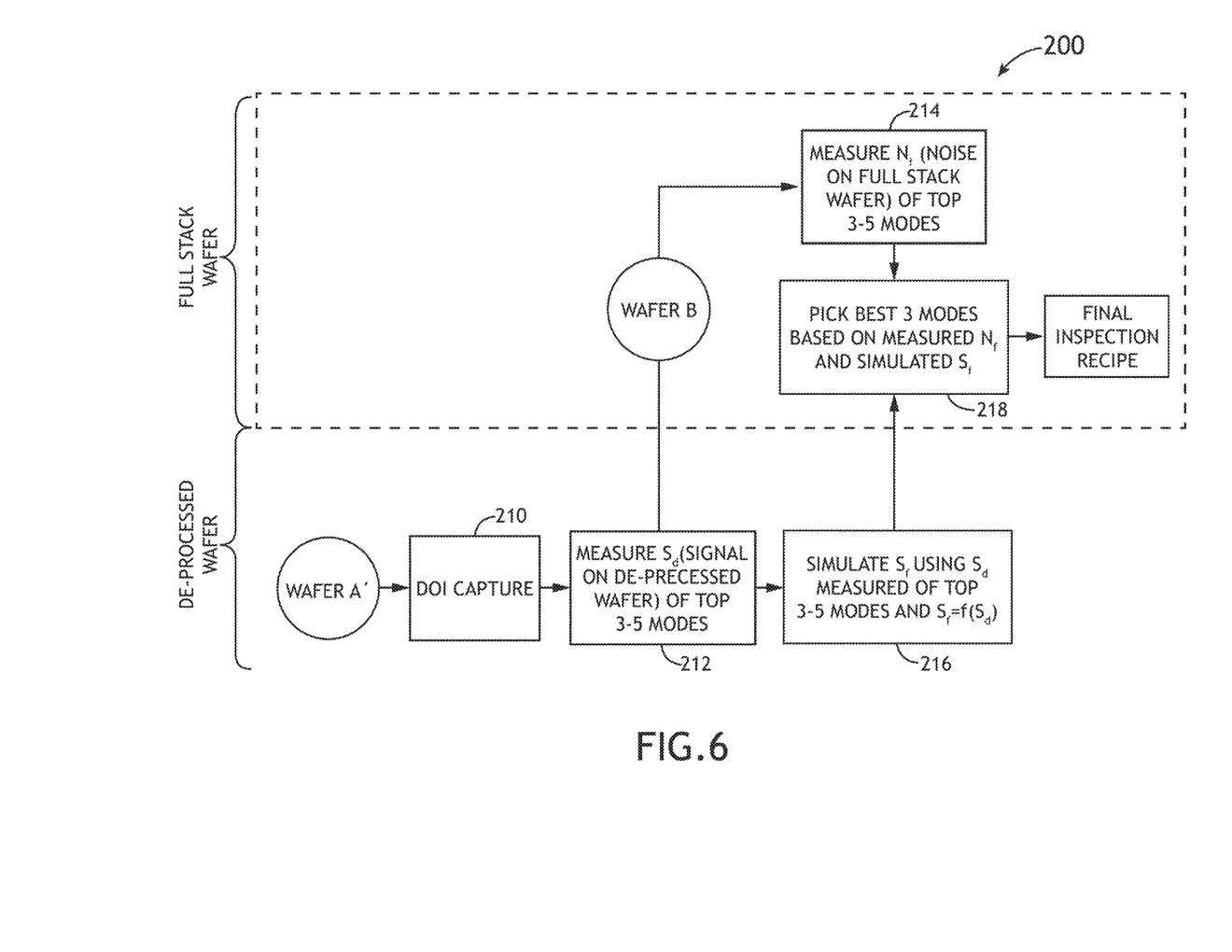
FIG. 6 is a flow diagram depicting another inspection method configured in accordance with an embodiment of the present disclosure.

It is contemplated that the inspection recipes obtained in this manner may be further refined using a simulation process as shown in FIG. 6. More specifically, a simulation step 216 may be utilized to simulate signals that would be obtained if the top N-number of optical modes identified by the step 212 were used to measure the wafer A before the wafer A was de-processed (i.e., when wafer A was still a full-stack wafer). The signals simulated in this manner may be denoted as Simulated S$_f$, which can be obtained based on the S$_d$ measured in the step 212 and the correlation S$_f$=f(S$_d$) established in the step 208. In other words, the step 216 effectively combines the correlation and the simulation together to produce the Simulated S$_f$, allowing the Simulated S$_f$ (representing the signal) to be used together with the measured N$_f$ (representing the noise) in a step 218 to further limit the selection of optical modes.

In some embodiments, the step 218 may be configured to only select the top M-number (where M≤N) of optical modes based on their S/N ratios. The effectiveness of the selected top M-number of optical modes may then be reviewed before final decisions are made. For instance, the selected top M-number of optical modes may be used to inspect the wafer B (or any full-stack wafer of the same type as the wafer A). The wafer B may then be de-processed to provide a de-processed wafer B', which may be reviewed to verify whether the selected top M-number of optical modes effectively detected the defects of interest. It is contemplated that the selected top M-number of optical modes may be recorded and/or reported as the final inspection recipe that can be utilized for subsequent inspections of wafers having the same type as the wafer A.

As will be appreciated from the above, the inspection method 200 described above can be utilized to quickly and accurately select the optical modes suitable for a given type of wafer without having to rely on a time consuming trial and error (or blind search) based approach. It is also noted that while the optical modes are the focus of the discussion above, inspection methods configured in accordance with embodiments of the present disclosure are not limited to optical mode selection only. In some embodiments, for example, the recipe tuning step 207 may also adjust/tune the algorithms used to process the optical images obtained in addition to (or instead of) the adjustment of the optical modes.

More specifically, in addition to (or instead of) performing the correlation step 208 (as previously described), a signal and noise measurement step may be invoked to measure the signal and noise on the identified DOI locations. Subsequently, the algorithms (e.g., filters) used to process the optical images obtained using the various optical modes may be analyzed/optimized and an optical mode that best captured the DOI may be selected. It is contemplated that the selected optical mode may be tuned, and the result may be recorded and/or reported as the final inspection recipe that can be utilized for subsequent inspections of wafers having the same type as the wafer A.

It is also contemplated that while the optical modes described above may differ in terms of aperture settings, focus settings, wavelength band, and/or frequency settings, not all three settings are required to be different. In some embodiments, for example, the aperture settings and the wavelength band may be fixed and the focus setting may be the only variable.

Figure 7:
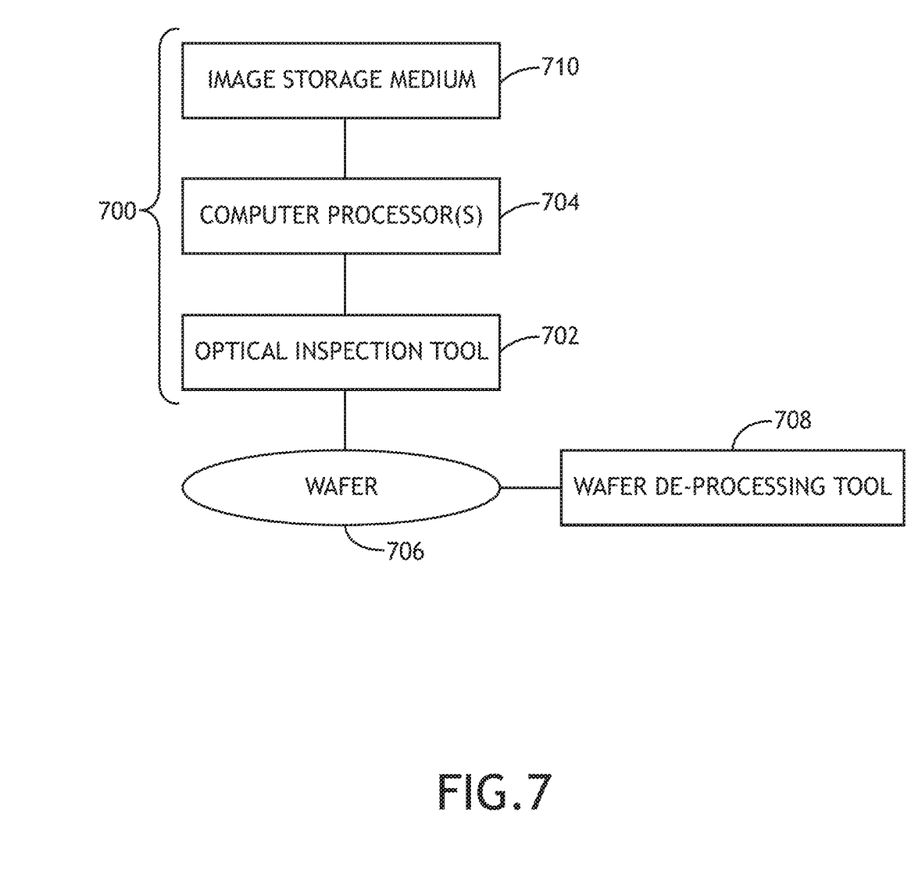
FIG. 7 is a block diagram depicting an inspection system configured in accordance with an embodiment of the present disclosure.

Referring now to FIG. 7, a block diagram depicting an inspection system 700 configured in accordance with embodiments of the present disclosure is shown. The inspection system 700 may include an optical inspection tool (may also be referred to as an optical inspector) 702 communicatively coupled to one or more computer processor(s) 704 and an image/data storage/recording medium 710 (e.g., computer-readable medium may be a storage medium such as a magnetic or optical disk, a magnetic tape, or any other suitable non-transitory computer-readable medium known in the art).

The optical inspection tool 702 may be configured to obtain optical images of a target (e.g., a wafer) 706 utilizing various optical modes. The optical inspection tool may be configured to store optical images on a storage medium 710. The processor 704 may be configured to receive the optical images obtained by the optical inspection tool 702 or from the image storage medium 710 and process the optical images as described above to help select one or more optical modes best suited for a given type of wafer. In some embodiments, the inspection system 700 may utilize a wafer de-processing tool (may also be referred to as a wafer de-processor) 708 to de-process a wafer during the optical mode selection process. Upon completion of the optical mode selection process, the optical inspection tool 702 may be configured to utilize the optical mode(s) selected and carry out the inspection accordingly.

It is contemplated that the processor 704 may be coupled to the optical inspection tool 702 in any suitable manner (e.g., via one or more transmission media, which may include "wired" and/or "wireless" transmission media) such that the processor 704 can receive the output generated by the optical inspection tool 702 or storage medium 710. The processor 704 may be configured to perform a number of functions using the output of the optical inspection tool 702 or storage medium 710. For instance, the processor 704 may be configured to detect defects on the specimen using the output of the optical inspection tool 702 or storage medium 710. Detecting the defects on the specimen may be performed by the processor 704 by applying some defect detection algorithm and/or method to the output generated by the optical inspection tool 702 or to the optical images on the storage medium 710. The defect detection algorithm and/or method may include any suitable algorithm and/or method known in the art. For example, the processor 704 may compare the output of the optical inspection tool 702 or storage medium 710 to a threshold. Any output having values above the threshold may be identified as a potential defect while any output having values below the threshold may not be identified as a potential defect. In another example, the processor 704 may be configured to send the output of the optical inspection tool 702 to a storage medium without performing defect detection on the output.

As noted above, the optical inspection tool 702 is configured to have multiple modes. In general, a "mode" can be defined by the values of parameters of the optical inspection tool 702 used to generate output of the specimen. Therefore, modes that are different may be different in the values for at least one of the optical parameters of the optical inspection tool 702. For example, in one embodiment in which the energy directed to the specimen and the energy detected from the specimen is light, at least one of the multiple modes uses at least one wavelength of the light directed to the specimen that is different from at least one wavelength of the light directed to the specimen for at least one other of the multiple modes. The modes may be different in the wavelength(s) of light directed to the specimen as described further herein (e.g., by using different light sources, different spectral filters, etc.) for different modes. In another embodiment, at least one of the multiple modes uses an illumination channel of the optical inspection tool 702 that is different from an illumination channel of the optical inspection tool 702 used for at least one other of the multiple modes. For example, the optical inspection tool 702 may include more than one illumination channel. As such, different illumination channels may be used for different modes.

In some embodiments, at least one of the multiple modes uses a configuration of an aperture of the optical inspection tool 702 that is different from a configuration of an aperture of the optical inspection tool 702 used for at least one other of the multiple modes. The aperture may be an illumination aperture (i.e., an aperture positioned in the path of the energy directed to the specimen) or a collection aperture (i.e., an aperture positioned in the path of the energy collected from the specimen) or both. For example, if energy is directed to the specimen in different paths for different modes, then different apertures having at least one different characteristic (e.g., shape or size) may be positioned in the different paths. In another example, if energy is directed to the specimen in the same path for different modes, then different apertures having at least one different characteristic may be positioned in the path at different times to sequentially generate images for the specimen. In similar manners, the aperture in the path of energy from the specimen may be different for different modes by having different apertures having at least one different characteristic in the path of different energy from the specimen or by switching the aperture in the path of the energy between different scans with different modes.

As described above, therefore, the different modes may be different in illumination or collection/detection or both. The different modes may also or alternatively have other differences in collection/detection. For example, in some embodiments, at least one of the multiple modes uses a detector of the optical inspection tool 702 that is different from a detector of the optical inspection tool 702 used for at least one other of the multiple modes. In some such embodiments, as described further above, the optical inspection tool 702 may include multiple detectors. Therefore, one of the detectors may be used for one mode and another of the detectors may be used for another mode. Furthermore, the modes may be different from each other in more than one way described herein (e.g., different modes may have one or more different illumination parameters and one or more different detection parameters). The multiple detectors may be used to detect different focal planes.

It is contemplated that the inspection system 700 may be implemented as a part of a defect review system and/or a metrology system. In some embodiments, the inspection system 700 may be configured to have a higher resolution if it is to be used for defect review or metrology rather than for general inspection. In other words, the embodiments of the inspection system 700 shown in FIG. 7 describe some general and various configurations for an inspection system that can be tailored in a number of manners that will be obvious to one skilled in the art to produce inspection systems having different imaging capabilities that are more or less suitable for different applications. In some embodiments, the inspection system may utilize scanning electron microscope (SEM) or optical inspection, or both, to carry out the inspection processes described above.

It is to be understood that while the examples above referred to wafers, the systems and methods in accordance with the present disclosure are applicable to other types of polished plates as well without departing from the spirit and scope of the present disclosure. The term wafer used in the present disclosure may include a thin slice of semiconductor material used in the fabrication of integrated circuits and other devices, as well as other thin polished plates such as magnetic disc substrates, gauge blocks and the like.

It is contemplated that the methods and systems described in the present disclosure may be implemented as standalone products or as components of various wafer measurement, inspection, and/or hotspot discovery tools. It is understood that the specific order or hierarchy of steps in the methods disclosed are examples of exemplary approaches. Based upon design preferences, it is understood that the specific order or hierarchy of steps in the method can be rearranged while remaining within the scope and spirit of the disclosure. It is also understood that the various blocks depicted in the figures are presented separately for illustrative purposes. It is contemplated that while the various blocks depicted in the figures may be implemented as separate (and communicatively coupled) devices and/or processing units, they may also be integrated together without departing from the spirit and the scope of the present disclosure.

It is believed that the system and the apparatus of the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory.

What is claimed is:

1. A method for selecting optical modes and algorithms suitable for defect inspection of a particular type of wafer, the method comprising:
scanning a full-stack wafer of the particular type utilizing a set of optical modes to obtain a set of full-stack wafer images; and
de-processing the full-stack wafer to produce a de-processed wafer based on a location of a potential defect of interest indicated by the set of full-stack wafer images to select optical modes and algorithms suitable for defect inspection of wafers of the particular type.

2. The method of claim 1, further comprising:
establishing a correlation between signals obtained from the full-stack wafer and verified defect locations on the de-processed wafer;
determining signal-to-noise ratios associated with the set of optical modes for verified defect locations;
selecting a subset of optical modes based on the signal or signal-to-noise ratios associated with the set of optical modes for the verified defect locations; and
forming a recipe for defect inspection based on the subset of optical modes selected.

3. The method of claim 1, further comprising:
scanning the de-processed wafer utilizing the set of optical modes to obtain a set of de-processed wafer images;
establishing a correlation between signals obtained from the full-stack wafer and signals obtained from the de-processed wafer based on the set of full-stack wafer images and the set of de-processed wafer images obtained;
determining signal-to-noise ratios associated with the set of optical modes utilizing the established correlation;
selecting a subset of optical modes based on the signal or signal-to-noise ratios associated with the set of optical modes; and
forming a recipe for defect inspection based on the subset of optical modes selected.

4. The method of claim 3, wherein said determining of signal or signal-to-noise ratios associated with the set of optical modes further comprises:
selecting top N-number of optical modes from the set of optical modes based on signal or signal-to-noise ratios associated with the set of optical modes when the set of optical modes is used to scan the de-processed wafer; and
measuring signals obtained from the de-processed wafer using the top N-number of optical modes.

5. The method of claim 4, wherein said determining of signal-to-noise ratios associated with the set of optical modes further comprises:
scanning the new full-stack wafer utilizing the top N-number of optical modes;
measuring an optical noise produced by the top N-number of optical modes; and
determining signal-to-noise ratios of the top N-number of optical modes.

6. The method of claim 5, wherein said selecting a subset of optical modes based on the signal-to-noise ratios associated with the set of optical modes further comprises:
selecting the subset of optical modes from the top N-number of optical modes based on the signal-to-noise ratios of the top N-number of optical modes.

7. The method of claim 6, further comprising:
scanning the new full-stack wafer utilizing the subset of optical modes selected;
de-processing the new full-stack wafer to produce a new de-processed wafer based on a location of a potential defect of interest indicated by said scanning the new full-stack wafer utilizing the subset of optical modes selected;
determining whether the subset of optical modes selected is effective in detecting defects; and
forming the recipe for defect inspection based on the subset of optical modes selected when the subset of optical modes selected is determined to be effective in detecting defects.

8. The method of claim 4, wherein said determining of signal or signal-to-noise ratios associated with the set of optical modes further comprises:
simulating signals that can be obtained from a new full-stack wafer using the top N-number of optical modes based on the signals obtained from the de-processed wafer using the top N-number of optical modes and the established correlation; and
selecting top M-number of optical modes from the top N-number of optical modes based on the signal or signal-to-noise ratios of the top N-number of optical modes.

9. The method of claim 8, wherein said determining of signal-to-noise ratios associated with the set of optical modes further comprises:
scanning the new full-stack wafer utilizing the top M-number of optical modes;
measuring an optical noise produced by the top M-number of optical modes; and
determining signal-to-noise ratios of the top M-number of optical modes.

10. The method of claim 9, further comprising:
scanning the new full-stack wafer utilizing the top M-number of optical modes;
de-processing the new full-stack wafer to produce a new de-processed wafer based on a location of a potential defect of interest indicated by said scanning the new full-stack wafer utilizing the top M-number of optical modes;
determining whether the top M-number of optical modes are effective in detecting defects; and
forming the recipe for defect inspection based on the top M-number of optical modes when the top M-number of optical modes is determined to be effective in detecting defects.

11. The method of claim 1, wherein the set of optical modes contains optical modes that differ in terms of aperture settings, focus settings, or wavelength band.

12. The method of claim 1, wherein the set of optical modes contains optical modes that differ only in terms of focus settings.

13. The method of claim 12, wherein the full-stack wafer images obtained include through-focus stack images of the full-stack wafer.

14. The method of claim 1, further comprising:
adjusting at least one algorithm utilized to process the full-stack wafer images obtained.

15. The method of claim 14, wherein the at least one algorithm includes at least one filtering algorithm.

16. The method of claim 1, further comprising:
scanning the de-processed wafer utilizing the set of optical modes to obtain a set of de-processed wafer images;
establishing a correlation between signals obtained from the full-stack wafer and signals obtained from the de-processed wafer based on the set of full-stack wafer images and the set of de-processed wafer images obtained;
selecting top N-number of optical modes from the set of optical modes based on signal-to-noise ratios associated with the set of optical modes when the set of optical modes is used to scan the de-processed wafer;
measuring signals obtained from the de-processed wafer using the top N-number of optical modes;
simulating signals that can be obtained from a new full-stack wafer using the top N-number of optical modes based on the signals obtained from the de-processed wafer using the top N-number of optical modes and the established correlation;
scanning the new full-stack wafer utilizing the top N-number of optical modes;
measuring an optical noise produced by the top N-number of optical modes;
determining signal-to-noise ratios of the top N-number of optical modes;
selecting a subset of optical modes from the top N-number of optical modes based on the signal-to-noise ratios of the top N-number of optical modes; and
forming a recipe for defect inspection based on the subset of optical modes selected.

17. The method of claim 16, further comprising:
scanning the new full-stack wafer utilizing the subset of optical modes selected;
de-processing the new full-stack wafer to produce a new de-processed wafer based on a location of a potential defect of interest indicated by said scanning the new full-stack wafer utilizing the subset of optical modes selected;
determining whether the subset of optical modes selected is effective in detecting defects; and
forming the recipe for defect inspection based on the subset of optical modes selected when the subset of optical modes selected is determined to be effective in detecting defects.

18. A system, comprising:
an optical inspection tool configured to obtain optical images of one or more wafers utilizing one or more optical modes;
an image storage medium; and
at least one processor in communication with the optical inspection tool, the at least one processor configured to facilitate selection of optical modes suitable for defect inspection, the at least one processor further configured to:
receive a set of full-stack wafer images obtained by the optical inspection tool by scanning a full-stack wafer using a set of optical modes;
receive verified defect locations based on at least one of an optical inspection or a scanning electron microscope review of a de-processed wafer, the de-processed wafer being a product of de-processing the full-stack wafer based on a location of a potential defect of interest indicated by the set of full-stack wafer images; and
form a recipe for defect inspection to be utilized by the optical inspection tool based on the set of full-stack wafer images and the verified defect locations from the de-processed wafer.

19. The system of claim 18, wherein the set of optical modes contains optical modes that differ in terms of aperture settings, focus settings, or wavelength band.

20. The system of claim 18, wherein the set of optical modes contains optical modes that differ only in terms of focus settings.

21. The system of claim 18, wherein the at least one processor is further configured to adjust at least one algorithm utilized to process the full-stack wafer images obtained.

22. A system, comprising:
an optical inspection tool configured to obtain optical images of one or more wafers utilizing one or more optical modes;
an image storage medium; and
at least one processor in communication with the optical inspection tool, the at least one processor configured to facilitate selection of optical modes suitable for defect inspection, the at least one processor further configured to:
receive a set of full-stack wafer images obtained by the optical inspection tool by scanning a full-stack wafer using a set of optical modes;
receive a set of de-processed wafer images obtained by the optical inspection tool by scanning a de-processed wafer using the set of optical modes, the de-processed wafer being a product of de-processing the full-stack wafer based on a location of a potential defect of interest indicated by the set of full-stack wafer images; and
form a recipe for defect inspection to be utilized by the optical inspection tool based on the set of full-stack wafer images and the set of de-processed wafer images.

23. The system of claim 22, wherein the at least one processor is further configured to:
establish a correlation between signals obtained from the full-stack wafer and signals obtained from the de-processed wafer based on the set of full-stack wafer images and the set of de-processed wafer images obtained;
determine signal-to-noise ratios associated with the set of optical modes utilizing the established correlation;
select a subset of optical modes based on the signal-to-noise ratios associated with the set of optical modes; and
form the recipe for defect inspection to be utilized by the optical inspection tool based on the subset of optical modes selected.

24. The system of claim 23, wherein the at least one processor is configured to determine signal or signal-to-noise ratios associated with the set of optical modes by:
select top N-number of optical modes from the set of optical modes based on signal or signal-to-noise ratios associated with the set of optical modes when the set of optical modes is used to scan the de-processed wafer; and
measure signals obtained from the de-processed wafer using the top N-number of optical modes.

25. The system of claim 24, wherein the optical inspection tool is further configured to scan the new full-stack wafer utilizing the top N-number of optical modes, and wherein the at least one processor is further configured to:

measure an optical noise produced by the top N-number of optical modes;
determine signal-to-noise ratios of the top N-number of optical modes; and
select the subset of optical modes from the top N-number of optical modes based on the signal-to-noise ratios of the top N-number of optical modes.

26. The system of claim 25, wherein the optical inspection tool is further configured to scan the new full-stack wafer utilizing the subset of optical modes selected, and wherein the at least one processor is further configured to:
determine whether the subset of optical modes selected is effective in detecting defects; and
form the recipe for defect inspection to be utilized by the optical inspection tool based on the subset of optical modes selected when the subset of optical modes selected is determined to be effective in detecting defects.

27. The system of claim 24, wherein the at least one processor is further configured to facilitate determination of signal or signal-to-noise ratios associated with the set of optical modes by:
simulate signals that can be obtained from a new full-stack wafer using the top N-number of optical modes based on the signals obtained from the de-processed wafer using the top N-number of optical modes and the established correlation; and
select top M-number of optical modes from the top N-number of optical modes based on the signal-to-noise ratios of the top N-number of optical modes.

28. The system of claim 27, wherein the optical inspection tool is further configured to scan the new full-stack wafer utilizing the top M-number of optical modes, and wherein the at least one processor is further configured to:
measure an optical noise produced by the top M-number of optical modes; and
determine signal-to-noise ratios of the top M-number of optical modes.

29. The system of claim 28, wherein the optical inspection tool is further configured to scan the new full-stack wafer utilizing the top M-number of optical modes, and wherein the at least one processor is further configured to:
determine whether the top M-number of optical modes are effective in detecting defects; and
form the recipe for defect inspection to be utilized by the optical inspection tool based on the top M-number of optical modes when the top M-number of optical modes is determined to be effective in detecting defects.

30. The system of claim 22, wherein the set of optical modes contains optical modes that differ in terms of aperture settings, focus settings, or wavelength band.

31. The system of claim 22, wherein the set of optical modes contains optical modes that differ only in terms of focus settings.

32. The system of claim 22, wherein the at least one processor is further configured to adjust at least one algorithm utilized to process the full-stack wafer images obtained.

* * * * *